United States Patent [19]

Sakagami

[11] Patent Number: 5,192,505
[45] Date of Patent: Mar. 9, 1993

[54] AUTOMATIC ANALYZING APPARATUS

[75] Inventor: Toshio Sakagami, Chofu, Japan

[73] Assignee: Olympus Optical Co., Ltd., Tokyo, Japan

[21] Appl. No.: 510,882

[22] Filed: Apr. 18, 1990

[30] Foreign Application Priority Data

Apr. 25, 1989 [JP] Japan .................. 1-103458

[51] Int. Cl.⁵ .............................. G01N 21/00
[52] U.S. Cl. ...................... 422/64; 422/67; 422/63
[58] Field of Search .......... 422/64, 63, 65, 67; 436/43, 45, 47, 48

[56] References Cited

U.S. PATENT DOCUMENTS

| | | | |
|---|---|---|---|
| 4,406,547 | 9/1983 | Aihara | 356/414 |
| 4,457,893 | 7/1984 | Takekawa | 422/64 |
| 4,522,921 | 6/1985 | Ogawa | 422/64 |
| 4,699,766 | 10/1987 | Yamashita | 422/64 |
| 4,785,407 | 11/1988 | Sakagami | 356/246 |
| 4,808,380 | 2/1989 | Minekane | 422/64 |
| 4,837,159 | 6/1989 | Yamada | 422/64 |
| 4,908,186 | 3/1990 | Sakamaki | 422/67 |

FOREIGN PATENT DOCUMENTS 3639399 5/1987 Fed. Rep. of Germany ...... 364/497

Primary Examiner—Douglas W. Robinson
Assistant Examiner—Theresa A. Trembley
Attorney, Agent, or Firm—Stevens, Davis, Miller & Mosher

[57] ABSTRACT

An automatic analyzing apparatus for analyzing biochemical samples such as blood and urine in which a disposable type reaction line and a reusable type reaction line are provided, so that items suitable for being analyzed by using the disposable reaction line, such as items to be analyzed by utilizing immunization agglutination reaction, can be analyzed in the disposable type reaction line, and items suitable for being analyzed by the reusable reaction line, such as items to be analyzed by colorimetric method, can be analyzed in the reusable type reaction line, simultaneously. Furthermore, these two types of analyzing lines are driven by only one driving device, the apparatus does not become complex in construction, large in size and expensive in cost although two reaction lines are provided.

5 Claims, 3 Drawing Sheets

FIG._1

AUTOMATIC ANALYZING APPARATUS

BACKGROUND OF THE INVENTION

1. Field of the Invention and Related Art Statement

The invention relates to an automatic analyzing apparatus for automatically analyzing biochemical samples such as blood and urine by measuring various kinds of substances contained in test liquid, i.e. a mixture of the sample and a reagent. There are suggested two types of automatic analyzing apparatus for analyzing such samples. One of them is a disposable type apparatus in which reaction vessels are disposed of from a reaction line every time one test liquid has been analyzed and new reaction vessels are changed therefor. The other one is a reusable type apparatus in which the reaction vessels set on the reaction line are used repeatedly by cleaning the reaction vessels after each analysis the test liquid.

When test items are to be analyzed by utilizing immunization agglutination reaction (hereinafter called as "immunization items"), the analysis is conducted by measuring the turbidity of the test liquid which becomes turbid by the antibody-antigen complex formed in the test liquid. The agglutinated antigen-antibody complex in the test liquid is apt to remain in the reaction vessel even if the reaction vessels are washed well. In addition to this, when measuring the turbidity of the test liquid containing the antigen-antibody complex, an S/N of an electric signal derived therefrom is so small that the agglutinated antigen-antibody complex remained in the reaction vessel affects a next analysis remarkably. Therefore, the disposable type analyzing apparatus is generally used for analyzing the immunization items.

On the other hand, in the reusable analyzing apparatus, the reaction vessels are used repeatedly by washing the reaction vessels every after each analysis operation. Therefore, it is very difficult to perfectly prevent the carry over of the test liquids in the reaction vessels. In order to prevent the carry over of the test liquid, it is necessary to provide many reaction vessel cleaning positions in the apparatus and/or to use cleaning material when washing the reaction vessels. Thus, the apparatus may become large in size and high in cost for analyzing.

When analyzing items to be analyzed by colorimetric method (hereinafter called "general items"), no agglutination occurs in the test liquid, and thus the test liquid is not apt to be carried over the reaction vessels after washing the reaction vessels. In addition to this, the signal-to-noise ratio (S/N) of the signal obtained by measuring the absorbency of the test liquid is so comparatively large that the carry over of the test liquid does not affect the S/N of the signal so much even if the test liquid is remained in the reaction vessels. If the disposable type analyzing apparatus is used for analyzing the general item, the cost for the reaction vessels becomes relatively high and thus the running cost for analyzing as a whole is increased. It also should be noted that the reagent for use in analyzing the general items is comparatively cheap, and thus the cost of the reaction vessel in the whole analyzing cost becomes high. For this reason, the reusable type analyzing apparatus is generally used for analyzing the general items.

Hitherto, these disposable and reusable analyzing apparatuses have been separately manufactured by maker and independently used by users. However, provided that the user have to provide these two type apparatuses separately, the cost for analyzing becomes high and a wide space for setting up the two apparatuses is necessary. Even if the disposable analyzing unit and the reusable analyzing unit are merely set up in one analyzing apparatus, the apparatus would become complex in construction and expensive in cost because two independent driving systems are necessary to drive the two reaction lines in the units.

SUMMARY OF THE INVENTION

The present invention has for its object to provide a novel automatic analyzing apparatus in which a reusable reaction line for use in analyzing the general items and a disposable reaction line for use in analyzing the immunization items, which are driven by one driving system and can be selectively used in accordance with the purpose of the analyzing.

It is another object of the invention to provide an analyzing apparatus which can decrease the cost for analyzing, and can prevent the carry over of the test liquids.

It is still another object of the invention to provide an analyzing apparatus which can be made simple in construction and small in size although the apparatus includes two reaction lines.

In order to carry out the above mentioned object, an automatic analyzing apparatus according to the invention comprises:

a first reaction line on which a plurality of reaction vessels are mounted in a disposable manner;

a second reaction line on which a plurality of reaction vessels are mounted in a reusable manner;

transportation means for transporting the reaction vessels mounted on said first and second reaction lines to a reaction vessel supply position, a sample delivery position, a reagent delivery position, a photometering position, a reaction vessel cleaning position and a disposing position;

reaction vessel supply mean for supplying reaction vessels to said first reaction line at the reaction vessel supply position;

sample delivery means for delivering a sample into at least one reaction vessel mounted on at least one of said first and second reaction lines at the sample delivery position in accordance with at least one test item to be analyzed for the relevant sample;

reagent delivery means for delivering reagents into the vessels mounted on said first and second reaction lines at the reagent delivery position in accordance with items to be analyzed;

photometering means for measuring given substances contained in test liquids contained in the reaction vessels mounted on the first and second reaction liens at the photometering position, each of said test liquids being a mixture of a sample and a reagent;

reaction vessel cleaning means for cleaning the reaction vessels mounted on the second reaction line at the reaction vessel cleaning position; and reaction vessel disposing means for disposing the reaction vessels mounted on the first reaction line at the disposing position.

As stated above, in the automatic analyzing apparatus according to the invention, the first and second reaction lines are provided in one analyzing apparatus, and one of the reaction lines is used as a disposable reaction line and the other is used as a reusable reaction line. Therefore, it is possible to use properly these two reaction lines in accordance with the purpose of the analyzing, for example, the disposable reaction line is used for analyzing immunization items and the reusable reaction line is used for analyzing general items. Further, since the reaction vessels mounted on these reaction lines are transported along these reaction lines by a common transportation means, the automatic analyzing apparatus can be made small in size and simple in overall construction while including both the disposable reaction line and reusable reaction line.

DETAILED DESCRIPTION OF THE PREFERRED EMBODIMENT

Figure 1:
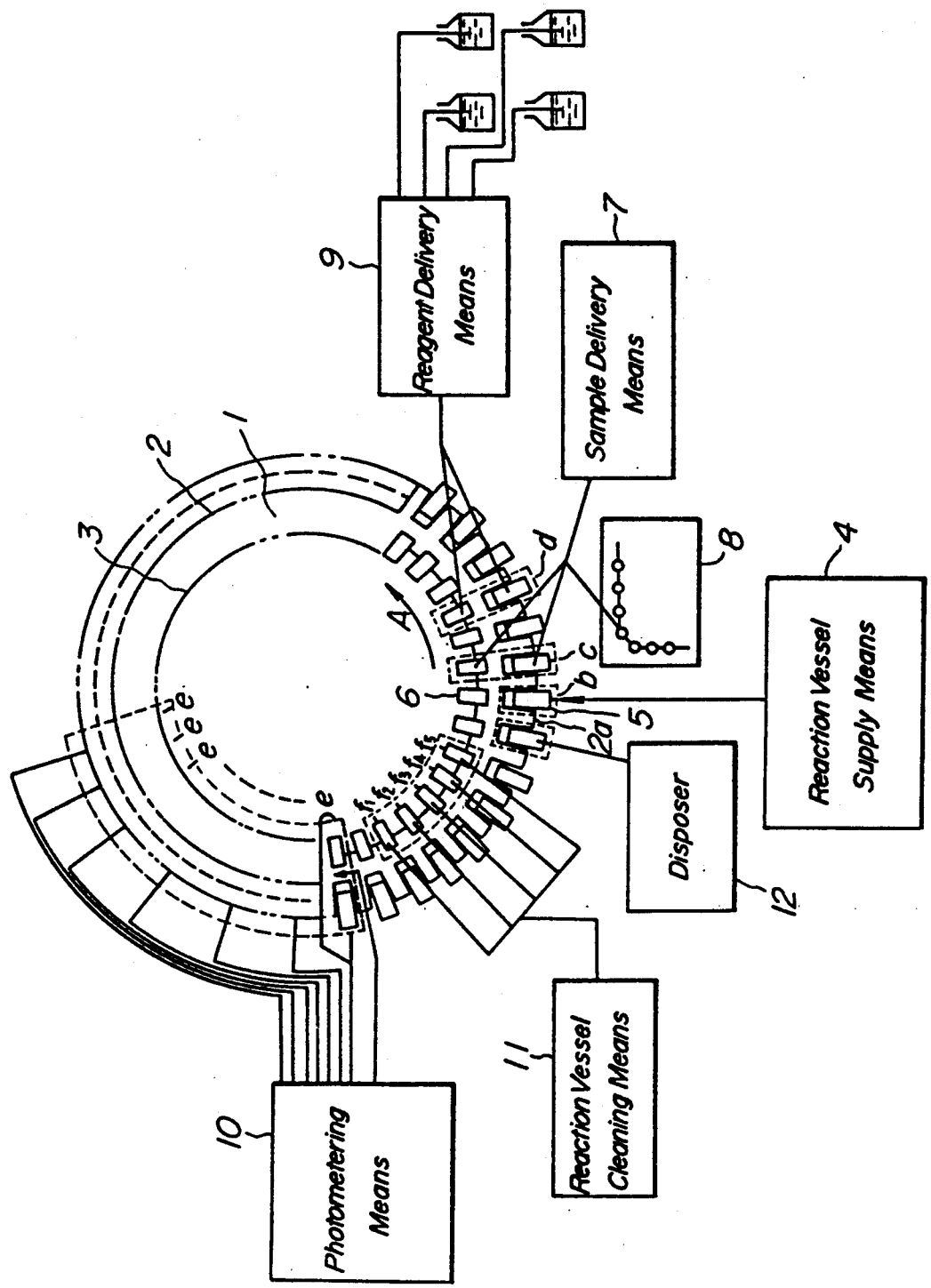
FIG. 1 is a schematic plan view showing a first embodiment of the automatic analyzing apparatus according to the present invention.

FIG. 1 is a schematic plan view showing a first embodiment of the automatic analyzing apparatus according to the present invention.

As shown in FIG. 1, the apparatus comprises a turntable 1 having a plurality of recesses on its circumferential edge. The turntable 1 is arranged to be intermittently rotated in a direction shown by an arrow A. In the recesses are detachably inserted reaction vessels 5 to form a disposable reaction line (first reaction line). This disposable reaction line is used for analyzing items to be analyzed by measuring the turbidity of the test liquid in which antigen-antibody complex is formed or for analyzing items to be analyzed by detecting an agglutinating reaction of solid phase carrier of antigen or antibody.

On the turntable 1, there is provided a reusable reaction line 3 (second reaction line) in a concentrical circle a little inner from the circumferential edge of the turntable 1. There are also mounted a plurality of reaction vessels 6 which are arranged not to be detachable. The number of the reaction vessels mounted on the second reaction line 3 is the same as that of the first reaction line 2. The reusable reaction line 3 is used for analyzing the general biochemical items which are analyzed by calorimetric method.

Analyzing in these disposable and reusable reaction lines is conducted in the following manner. The turntable 1 is arranged to be intermittently rotated into the direction shown by the arrow A and around which a plurality of functional positions, such as a reaction vessel supply position b, a sample delivery position c, a reagent delivery position d, photometering positions e and reaction vessel cleaning positions f are provided. At a reaction vessel supply position b on the first reaction line 2, disposable reaction vessels 5 are successively mounted into said recesses 2a arranged on the first reaction line 2 of the turntable 1 by a reaction vessel supply device 4. At the next position c arranged on the first and second reaction lines 2 and 3, samples such as blood and urine are delivered into the disposable reaction vessels 5 mounted on the first reaction line 2 and the reusable reaction vessels 6 provided on the second reaction line 3 by means of a sample delivery device 7. The numerical number 8 denotes a sample transportation device. Further, at the next position d, a necessary reagent is delivered into the reaction vessels 5 and 6 in accordance with the items to be analyzed. Thereafter, at a plurality of photometering positions e, the turbidity of the test liquid, i.e. the mixture of the sample and the reagent which have been reacted in the reaction vessels 5 and 6, are measured by means of a photometering device 10. After measuring, the reusable reaction vessels 6 of the second reaction line 3 are washed at cleaning positions $f_1 \sim f_5$ by means of the reaction vessel cleaning device 11. After cleaning the reusable reaction vessels 5 Of the second reaction line 3, the reaction vessels 5 and 6 are transported to the last functioning position g and then the disposable reaction vessels 5 are disposed of by means of a disposer 12 at this position g.

As stated above, in the first reaction line 2, new reaction vessels 5 are supplied by the reaction vessel supplying device 4 into empty recesses 2a. Therefore, in the first reaction line 2, the carry over of the test liquid is completely prevented.

In the second reaction line 3, the reaction vessels 6 are cleaned by means of the reaction vessel cleaning device 11, after each photometering operation the absorbency of the test liquid, so that the reaction vessels mounted on the second reaction line 3 can be used repeatedly. Therefore, in the second reaction line 3 the cost for reaction vessels can be saved.

In the analyzing apparatus according to the invention, the samples and the reagents are delivered into the reaction vessels 5 and 6 of the first and second reaction lines 2 and 3 by using the sample delivery device 7 and the reagent delivery device 9 which are commonly used for the two reaction lines, and the turntable 1 commonly serves to transport the reaction vessels mounted on the first and second reaction lines 2 and 3. Therefore, the analyzing apparatus does not become big in size while the apparatus comprises two reaction lines 2 and 3.

Figure 2:
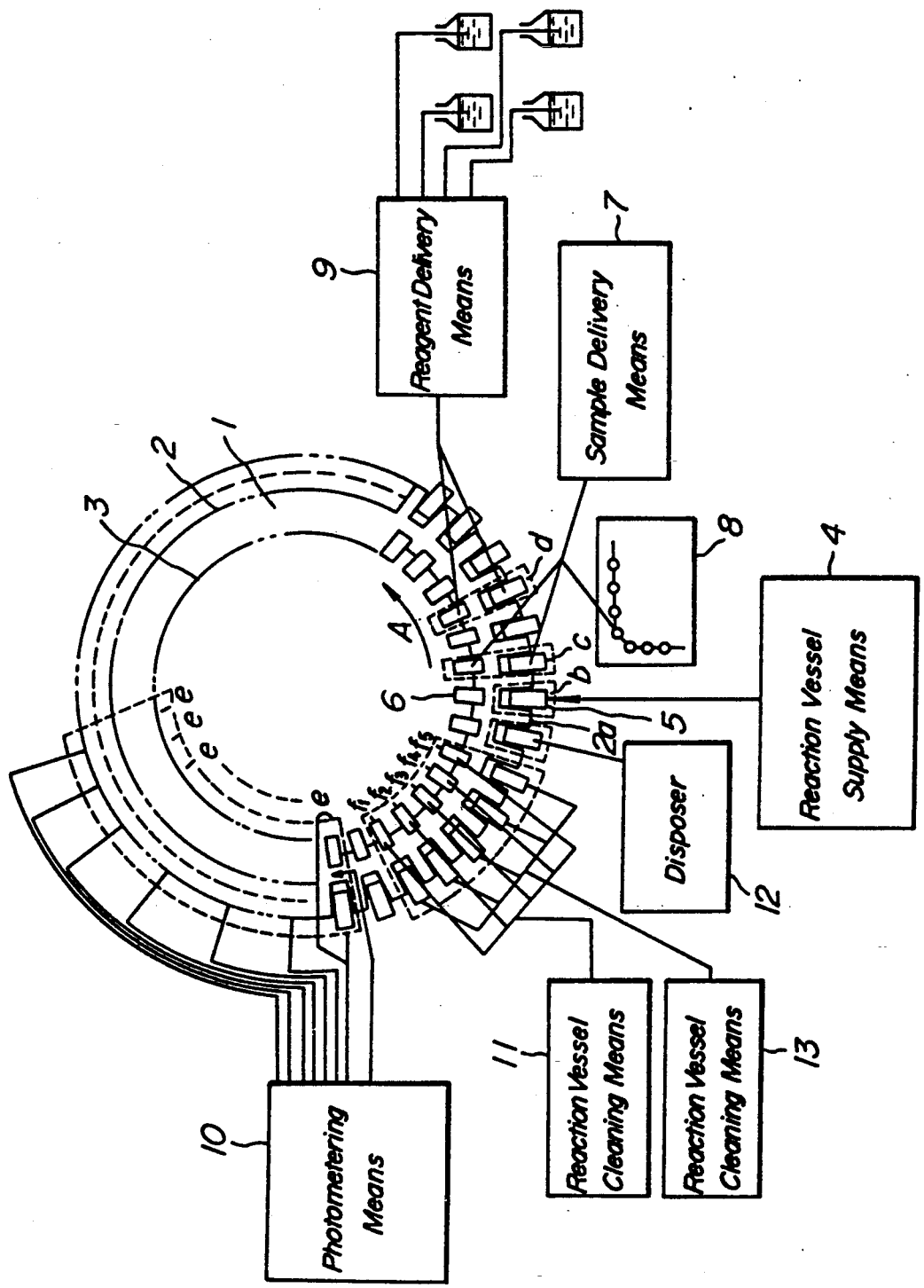
FIG. 2 is a schematic plan view depicting a second embodiment of the automatic analyzing apparatus according to the present invention.

FIG. 2 is a schematic plan view depicting the second embodiment of the automatic analyzing apparatus according to the invention. In the second embodiment, there is further provided a reaction vessel cleaning device 13 having the same construction as that of the cleaning device 11 on the first (disposable) reaction line 2, so that it is possible to selectively use the first reaction line 2 as disposable or reusable. The other construction of the analyzing apparatus is the same as that of the first embodiment.

Figure 3:
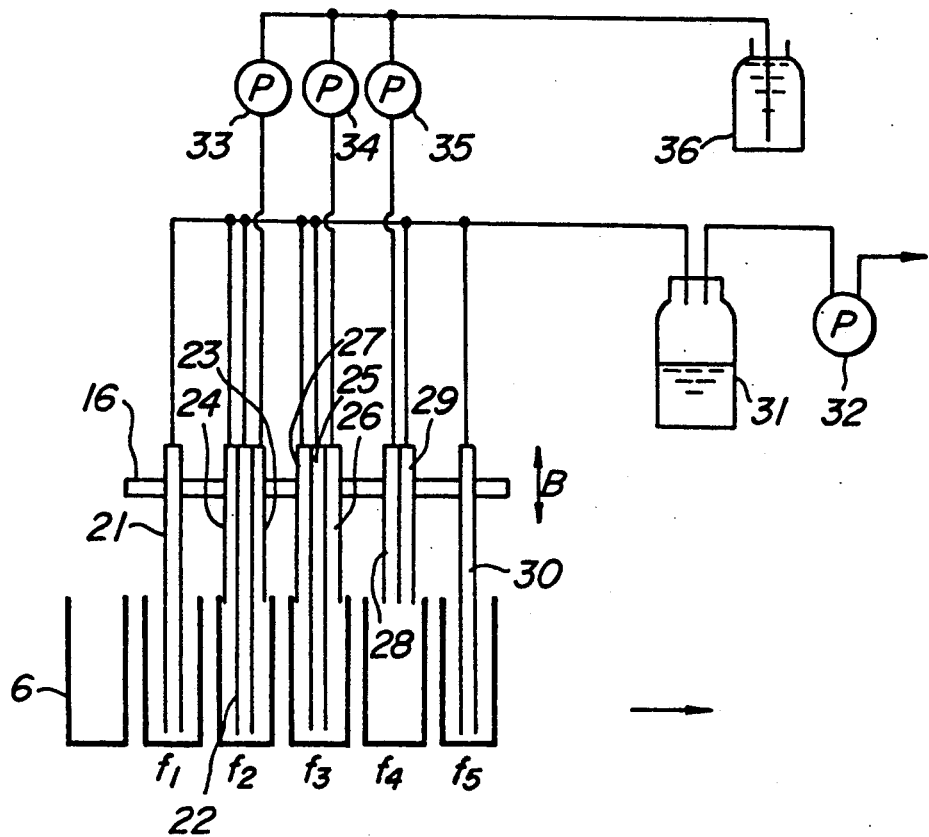
FIG. 3 is a schematic view representing a detail construction of a reaction vessel cleaning device which is provided in the apparatus according to the invention.

FIG. 3 is a schematic view representing the detail construction of the reaction vessel cleaning device 11. After photometering, the reaction vessel 6 is intermittently transported in the direction shown by an arrow A in FIGS. 1 and 2 and stopped at the positions $f_1 \sim f_5$, successively. At the position $f_1$, is provide an exhaust nozzle 21; at the position $f_2$, an exhaust nozzle 22, liquid supply nozzle 23 and an overflow nozzle 24; at the position $f_3$, an exhaust nozzle 25, liquid supply nozzle 26 and an overflow nozzle 27; at the position $f_4$, a liquid supply nozzle 28 and an overflow nozzle 29; and at the position $f_5$, an exhaust nozzle 30 is provided. The nozzle $21 \sim 30$ are connected to a holder 16 which is arranged to be movable in a vertical direction shown by an arrow B in FIG. 3. Thus, these nozzles $21 \sim 30$ are controlled to be moved up and down in conjunction with the movement of the reaction vessel 6. The exhaust nozzles 21, 22, 25 and 30 and the overflow nozzles 24, 27 and 29 are connected to a vacuum pump 32 via a bottle 31 into which the liquid sucked by these nozzles are exhausted. The liquid supply nozzles 23, 26 and 28 are connected to the washing liquid tank 36 via liquid supply pumps 33, 34, 35, respectively.

When the reaction vessel 6 is stopped at the position $f_1$, the holder 16 comes down and the exhaust nozzle 21 exhausts the test liquid in the reaction vessel 6. And, at the position $f_2$, the liquid supply nozzle 23 supplies the washing liquid in the vessel 6 and thereafter the washing liquid in the vessel 6 is exhausted by the exhaust nozzle 22 and the overflow nozzle 24. Further at the position $f_3$, the liquid supply nozzle 24 supplies the washing liquid again, the washing liquid is exhausted by the exhaust nozzle 25 and the overflow nozzle 27. Thereafter, at the position $f_4$, the reaction vessel 6 is filled with the washing liquid by means of the liquid supply nozzle 28 and the overflow nozzle 29, and at the position $f_5$, the exhaust nozzle 30 exhausts the washing liquid in the reaction vessel 6 to finish the cleaning process.

Figure 4:
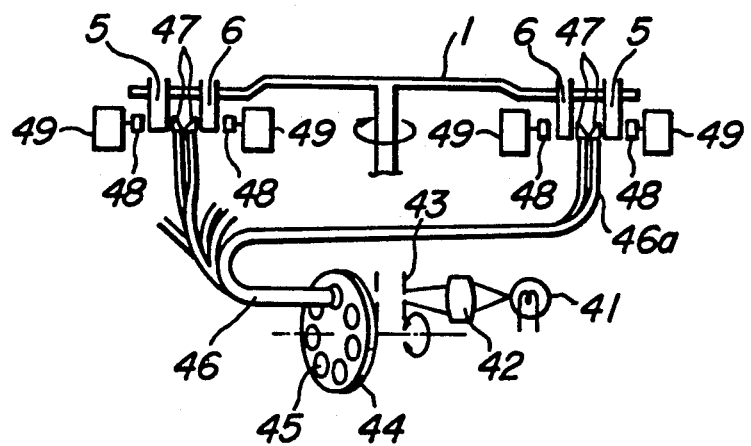
FIG. 4 is a schematic view illustrating a photometering device which is provided in the apparatus according to the invention.

FIG. 4 is a schematic view illustrating the photometer 10 which is adapted to the analyzing apparatus according to the invention.

In the photometer 10, white light emitted from a light source 41 is introduced to a slit 43 via a lens 42. In an optical path of the light exiting from the slit 43, there is rotatably arranged a filter ring 44 in which a plurality of interference filters 45 are provided. By rotating the filter ring 44, the proper interference filter is selected to transmit light having a proper wavelength for analyzing the test liquid in the reaction vessels 5 and 6. The light beam having the proper wavelength for analyzing is introduced into an optical fiber bundle 46 branching into a plurality of optical fibers. Each pairs of exiting ends 46a of the optical fibers are extended to each measuring positions e to introduce the light beams into prisms 47, 47 arranged between the reaction vessels 5 and 6. The light beams are reflected by the prisms 47, 47 and made incident upon the vessels 5 and 6. Each light beams which have been passed through the reaction vessels 5 and 6 are received by light receiving elements 48, 48 to measure the absorbency of the test liquids. The photoelectric conversion outputs of the light receiving elements 48, 48 are amplified by amplifiers 49, 49 and then supplied to the calculating device (not shown) to obtain the absorbency of the test liquids.

In the embodiments mentioned above, the turntable 1 is used as the means for transporting the reaction vessels mounted on the reaction lines, but it should be noted that any transportation means having endless reaction lines can be used therefor.

In the first embodiment mentioned above, the immunization items are analyzed in the first reaction line and the general biochemical items are analyzed in the second reaction line. However, in case the carry over of the test liquids makes serious influence upon the analyzing result of the general items, it is possible to analyze the items in the first (disposal) reaction line. That is to say, in the analyzing apparatus according to the present invention, it is possible to select the proper reaction line in accordance with the carry over test liquids.

What is claimed is:

1. An automatic analyzing apparatus comprising:
   a first reaction line on which a plurality of first reaction vessels are detachably mounted to be disposable;
   a second reaction line on which a plurality of second reaction vessels are non-detachably mounted to be reusable;
   a common transportation means for transporting the first and second reaction vessels respectively mounted on said first and second reaction lines to a reaction vessel supply position, a sample delivery position, a reagent delivery position, a photometering position, a reaction vessel cleaning position and a disposing position;
   reaction vessel supply means for supplying said first reaction vessels to said first reaction line at the reaction vessel supply position;
   sample delivery means for delivering a sample into at least one reaction vessel mounted on at least one of said first and second reaction lines at the sample delivery position in accordance with at least one test item to be analyzed for the relevant sample;
   reagent delivery means for delivering reagents into the vessels mounted on said first and second reaction lines at the reagent delivery position in accordance with items to be analyzed;
   photometering means for measuring given substances contained in test liquids contained in the reaction vessels mounted on the first and second reaction lines at the photometering position, each of said test liquids being a mixture of a sample and a reagent;
   first cleaning means for cleaning the second reaction vessels mounted on the second reaction line at the reaction vessel cleaning position; and
   reaction vessel disposing means for disposing the first reaction vessels mounted on the first reaction line at the disposing position.

2. An automatic analyzing apparatus according to claim 1, wherein:
   said apparatus further comprises second cleaning means for cleaning the first reaction vessels mounted on the first reaction lines, and said second cleaning means is arranged between said photometering position and said disposing position.

3. An automatic analyzing apparatus according to claim 1, wherein:
   said transportation means comprises a turntable in which the first reaction line and the second reaction line are concentrically provided.

4. An automatic analyzing apparatus according to claim 3, wherein:
   said first reaction line comprises a plurality of recesses which are formed in a circumferential edge of the turntable, and the first reaction vessels are detachably inserted in said recesses.

5. An automatic analyzing apparatus according to claim 1, wherein said first reaction line includes only reaction vessels which constitute said first reaction vessels which are detachably mounted so as to disposable, and said second reaction line includes only reaction vessels which constitute said second reaction vessels which are non-detachably mounted to be reusable.

* * * * *